US008504392B2

(12) United States Patent
Saria et al.

(10) Patent No.: US 8,504,392 B2
(45) Date of Patent: Aug. 6, 2013

(54) AUTOMATIC CODING OF PATIENT OUTCOMES

(75) Inventors: Suchi Saria, New York, NY (US); Gayle McElvain, Palo Alto, CA (US); Anand K. Rajani, Fresno, CA (US); Anna A. Penn, Palo Alto, CA (US); Daphne L. Koller, Portola Valley, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 61 days.

(21) Appl. No.: 13/294,959

(22) Filed: Nov. 11, 2011

(65) Prior Publication Data

US 2012/0290319 A1 Nov. 15, 2012

Related U.S. Application Data

(60) Provisional application No. 61/412,770, filed on Nov. 11, 2010.

(51) Int. Cl.
*G06Q 50/00* (2006.01)

(52) U.S. Cl.
USPC ........ 705/3; 706/12; 706/25; 706/45; 706/47; 706/61

(58) Field of Classification Search
USPC ........................... 705/2–4; 706/12, 25, 45–61
See application file for complete search history.

(56) References Cited

U.S. PATENT DOCUMENTS

| | | | | |
|---|---|---|---|---|
| 8,024,128 | B2* | 9/2011 | Rabinowitz et al. | 702/19 |
| 8,126,736 | B2* | 2/2012 | Anderson et al. | 705/2 |
| 2004/0242972 | A1* | 12/2004 | Adak et al. | 600/300 |
| 2006/0173663 | A1* | 8/2006 | Langheier et al. | 703/11 |
| 2008/0133275 | A1* | 6/2008 | Haug et al. | 705/3 |
| 2008/0201280 | A1* | 8/2008 | Martin et al. | 706/12 |
| 2009/0276241 | A1* | 11/2009 | Haskell et al. | 705/2 |

OTHER PUBLICATIONS

Cannon, J. (2009). Perceptions of physician assistants in the U.S. coast guard on delivering healthcare services: A phenomenological study. University of Phoenix). ProQuest Dissertations and Theses, , 361. Retrieved from http://search.proquest.com/docview/304165370?accountid=14753. (304165370). Best ProQuest NPL result.*

Solt et al., "Semantic Classification of Diseases in Discharge Summaries Using a Context-aware Rule-based Classifier." J Am Med Inform Assoc., 16:580-584 (2009).

(Continued)

*Primary Examiner* — Mark Holcomb
(74) *Attorney, Agent, or Firm* — Knobbe Martens Olson & Bear LLP

(57) ABSTRACT

Systems and methods can mine structured clinical event data in an electronic health record (EHR) system to determine patient outcomes. Mining the structured clinical event data instead of or in addition to mining discharge summaries can increase the accuracy of patient outcome identification. Sophisticated language models can be used to extract outcomes from discharge summaries while also inferring outcomes from cues or hints contained in the structured clinical event data. For example, the clinical event data can include information regarding treatments and medications prescribed by clinicians to specifically manage patient complications; thus, presence or absence of relevant treatments in the clinical event data can provide independent indicators to disambiguate cases where current language processing approaches fail.

10 Claims, 8 Drawing Sheets

OTHER PUBLICATIONS

Friedman et al., "Automated encoding of clinical documents based on natural language processing." J Am Med Inform Assoc. 11(5):392-402 (2004).

Meystre et al., "Extracting Information from Textual Documents in the EHR: A Review of Recent Research." IMIA Yearbook of Medical Informatics, pp. 128-144 (2008).

Campbell et al., "A comparison of four schemes for codifications of problem lists." Proc Annu Symp Comput Appl Med Care, pp. 201-205 (1994).

Solti et al. "Building an Automated Problem List Based on Natural Language Processing: Lessons Learned in the Early Phase of Development." AMIA Annu Symp Proc., pp. 687-691 (2008).

Zhu et al., "Classification of gene microarrays by penalized logistic regression." Biostatistics 5(3):427-443 (2004).

Crammer et al., "Automatic Code Assignment to Medical Text." Proceedings of the Workshop on BioNLP, pp. 1-8 (2007).

Goldstein et al., "Three Approaches to Automatic Assignment of ICD-9-CM Codes to Radiology Reports." AMIA Annu Symp Proc., pp. 279-283 (2007).

Li et al., "Comparing ICD9-Encoded Diagnoses and NLP-Processed Discharge Summaries for Clinical Trials Pre-Screening: A Case Study." AMIA Annu Symp Proc., pp. 404-408 (2008).

Lafferty et al. "Conditional Random Fields: Probabilistic models for segmenting and labeling sequence data." ICML, pp. 1-8 (2001).

Uzuner, "Recognizing obesity and Co-morbidities in sparse data." J Am Med Inform Assoc., 16(4):561-571 (2009).

Burton et al., "Medication and Indication Linkage: A Practical Therapy for the Problem List?" AMIA Annu Symp Proc. 86-90 (2008).

Friedman et al., "Additive Logistic Regression: A Statistical View of Boosting." Technical Report, Dept. of Statistics, Stanford University, pp. 1-45 (1998).

\* cited by examiner

| Complication | M | E | C | R |
|---|---|---|---|---|
| Respiratory Distress Syn (RDS) | X | X | | |
| Sepsis | X | | | X |
| Patent Ductus Arteriosus (PDA) | X | X | | X |
| Bronchopulmonary Dysplapsia (BPD) | X | | | |
| Intraventricular Hemorrhage (IVH) | | | | |
| Died | | | | |
| Pneumothorax (PNE) | X | | | |
| Adrenal Insufficiency (ADR) | X | | | |
| Coagnegative Stahylococcus (BCS) | X | X | X | |
| Necrotizing Enterocolitis (NEC) | X | | X | X |
| Bacterinia (BAC) | | | | |
| Arrhythmia (ARR) | | | | |
| Hydrocephalus (HYD) | | | X | |
| Pulmonary Hemorrhage (PUL) | | | | |
| Urinary Tract Infection (UTI) | | | | |
| Adrenal Renal Failure (ARF) | | X | | |
| Pneumonia (PNA) | | | | |
| Pulmonary Hypertension (PPHN) | | | | |
| Seizure (SEI) | X | | | |
| Chronic Renal Failure (CRF) | | X | | |

FIG. 4

| Model | Feature Set | Prec. | Recall | F1 |
|---|---|---|---|---|
| DLM | All features | 73.5 | 86.1 | 79.4 |
| LLM | Disease Mentions | 88.7 | 72.8 | 79.9 |
| | + Negations | 90.7 | 78.2 | 83.9 |
| | + Uncertain | 90.8 | 77.8 | 83.7 |
| | + Correlated | 90.6 | 79.5 | 84.7 |

| Comp | Language Model | | | EHR Model | | |
|---|---|---|---|---|---|---|
| | Pr. | Re. | F1 | Pr. | Re. | F1 |
| RDS | 96.2 | 93.8 | 95.0 | 96.8 | 94.5 | 95.6 |
| SEPSIS | 82.3 | 69.8 | 75.5 | 92.5 | 79.5 | 85.5 |
| PDA | 92.4 | 85.6 | 88.9 | 94.7 | 87.0 | 90.7 |
| BPD | 90.5 | 73.3 | 81.0 | 92.9 | 82.2 | 87.2 |
| IVH | 92.9 | 79.0 | 85.4 | 96.2 | 78.5 | 86.5 |
| DIED | 95.0 | 93.9 | 94.5 | 94.7 | 93.7 | 94.2 |
| PNE | 100.0 | 85.9 | 92.4 | 100.0 | 84.1 | 91.4 |
| ADR | 90.4 | 56.8 | 69.8 | 91.4 | 64.2 | 75.4 |
| BCS | 93.6 | 88.6 | 91.0 | 99.7 | 87.5 | 93.2 |
| NEC | 76.5 | 59.5 | 66.9 | 74.6 | 61.5 | 67.4 |
| BAC | 69.6 | 11.3 | 19.5 | 100.0 | 68.6 | 81.3 |
| ARR | 98.5 | 50.2 | 66.5 | 98.1 | 61.0 | 75.2 |
| HYD | 88.3 | 79.7 | 83.8 | 88.8 | 91.2 | 90.0 |
| PUL | 100.0 | 99.5 | 99.8 | 100.0 | 90.5 | 95.0 |
| UTI | 59.0 | 58.5 | 58.7 | 55.7 | 57.0 | 56.3 |
| ARF | 67.7 | 28.2 | 39.8 | 71.2 | 33.3 | 45.4 |
| PNA | 100.0 | 2.0 | 4.0 | 100.0 | 2.7 | 5.3 |
| PPHN | 58.3 | 59.6 | 58.9 | 58.6 | 60.3 | 59.4 |
| SEI | 54.8 | 43.8 | 48.6 | 60.9 | 48.6 | 54.1 |
| ALL | 90.6 | 79.5 | 84.7 | 93.5 | 83.6 | 88.3 |

FIG. 6

AUTOMATIC CODING OF PATIENT OUTCOMES

RELATED APPLICATION

This application claims priority under 35 U.S.C. §119(e) to U.S. Provisional Application No. 61/412,770, filed Nov. 11, 2010, titled "Combining Structured and Free-Text Data for Automatic Coding of Patient Outcomes," the disclosure of which is hereby incorporated by reference in its entirety.

BACKGROUND

Patient interactions with health care providers are being digitized at a rapidly accelerated pace. In many cases, digital records of these interactions include data regarding early presentations of symptoms, sets of diagnostic tests administered and their results, passive monitoring results, series of interventions, and detailed reports of health progression by health practitioners. These records can be as simple as textual input or as detailed as video of a clinician-patient interaction. Consequently, the modern hospital tends to generate large volumes of data. With the recent ubiquity of electronic health record (EHR) databases, much, if not all, of this patient information is often documented within a single storage system.

Included in hospital EHR databases are discharge summaries that summarize the conditions, symptoms, and treatments of a patient during the patient's stay in a hospital. These discharge summaries include freeform text that can be mined programmatically using natural language processing techniques to classify the health conditions of the patient. The mined classifications can be used to facilitate medical billing for services rendered to the patient during his or her stay at the hospital. For example, the mined classifications can include medical billing codes, such as codes based on the International Statistical Classification of Diseases and Related Health Problems (commonly referred to as "ICD"). Versions of ICD classification codes often used by medical billing systems include ICD-9 and ICD-10 codes.

SUMMARY

Among other things, embodiments of systems and methods described herein integrate structured clinical event data such as medications, treatments, and laboratory results into current natural language processing systems that mine discharge summaries for billing codes. As a result, these systems and methods can significantly boost accuracy of billing code generation. The systems and methods described herein can open several exciting avenues for the processing of EHR data toward providing enhanced patient care in an efficient and cost-effective manner.

Certain aspects, advantages and novel features of the inventions are described herein. It is to be understood that not necessarily all such advantages may be achieved in accordance with any particular embodiment of the inventions disclosed herein. Thus, the inventions disclosed herein may be embodied or carried out in a manner that achieves or selects one advantage or group of advantages as taught herein without necessarily achieving other advantages as may be taught or suggested herein.

In several embodiments, a system for classifying a health condition of a patient includes: a model creation engine that can create a medical classification model by at least: receiving an identification of a clinical feature that is to be associated with a health condition, where the identification is provided by one or more of an automated analysis of an electronic medical reference and a manual expert identification of the clinical feature. The clinical feature can include one or more of the following features in some embodiments: an identified medication, a clinical event, a microbial culture feature, and a radiology feature. The model creation engine can also create a rule that maps the clinical feature to the health condition in a model data repository comprising physical computer storage. The rule can reflect a relationship between the clinical feature and the health condition. In addition, the model creation engine can automatically learn a weight to apply to the rule with a supervised machine learning algorithm by at least analyzing the clinical feature with respect to pre-identified outcomes in a training data set. The training data set can include first structured clinical event data. The rule can reflect a strength of the relationship between the clinical feature and the health condition. Further, the model creation engine can store, in the model data repository, the learned weight associated with the rule for subsequent usage in identifying a patient health condition. The system can also include an outcome identification module including computer hardware. The outcome identification module can at least access patient data corresponding to a patient, which includes second structured clinical event data stored in an electronic health record (EHR) database. The outcome identification module can also analyze the second structured clinical event data to determine whether the clinical feature exists in the clinical event data and can apply the rule and the weight of the medical classification model to the clinical feature to infer a possible health condition of the patient by at least matching the rule with a selected clinical feature in the second structured clinical event data corresponding to the patient. Moreover, the outcome identification module can provide one or more billing codes that can be processed by a medical billing system. The one or more billing codes can be based at least in part on the possible health condition of the patient.

A method of classifying a health condition of a patient includes, in several embodiments: receiving an identification of clinical features associated with one or more outcomes of patient care and storing rules in a model data repository. The rules can map the clinical features to the one or more outcomes. The method can further include using a machine learning process to automatically learn weights to apply to the rules by analyzing the clinical features with respect to known outcomes of patients stored in a training data set. The training data set can include first structured clinical event data in an electronic health record (EHR) system. The method may also include storing, in the model data repository, the learned weights together with the rules for subsequent inferring of possible outcomes of patient care from second structured clinical event data. At least said automatically learning the weights can be implemented by a computer system comprising computer hardware.

In some embodiments, non-transitory physical computer storage is provided having instructions stored therein for implementing, in one or more processors, operations for classifying a health condition of a patient. The operations can include: accessing patient data corresponding to a patient, where the patient data includes clinician notes associated with the patient and structured clinical event data stored in an electronic health record (EHR) data repository, analyzing the clinician notes to extract language features, analyzing the structured clinical event data to extract clinical features, and applying a probabilistic function to the language features and the clinician features to identify one or more possible outcomes associated with care of the patient.

A method of classifying a health condition of a patient can include, in some embodiments (and be implemented by a computer system having computer hardware): accessing patient data corresponding to a patient, the patient data having structured clinical event data stored in an electronic health record (EHR) data repository, analyzing the structured clinical event data to extract clinical features, and applying a probabilistic function to the clinician features to identify one or more outcomes associated with care of the patient.

BRIEF DESCRIPTION OF THE DRAWINGS

The features disclosed herein are described below with reference to the drawings. Throughout the drawings, reference numbers are re-used to indicate correspondence between referenced elements. The drawings are provided to illustrate embodiments of the inventions described herein and not to limit the scope thereof.

FIG. 4 illustrates an example table that lists certain complication-specific clinical features used by one embodiment of the medical classification system.

FIG. 6 illustrates another example table that compares performance of an embodiment of the medical classification system with another medical classification system.

DETAILED DESCRIPTION

I. Introduction

Figure 1A:
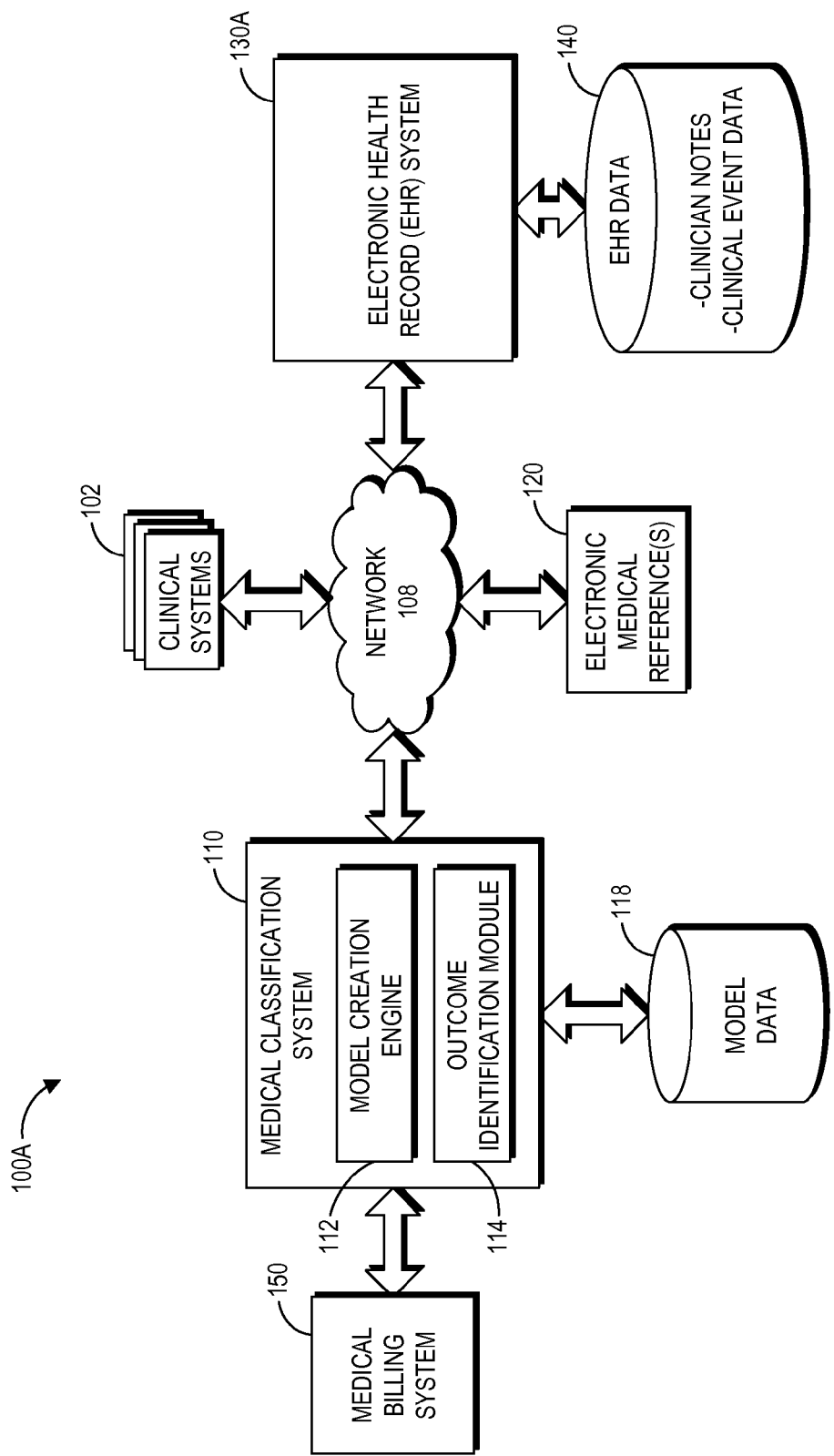
FIG. 1A illustrates an embodiment of a computing environment that can implement a medical classification system.

In addition to discharge summaries, EHR databases also include records of structured clinical event data for each patient. Much of this data is captured at a high degree of granularity. One example of structured clinical event data is continuous physiologic monitoring data. This data is often generated by bedside monitors, which may monitor such parameters as heart rate, respiratory rate, oxygen saturation, and blood pressure. The bedside monitors can provide verbose time-stamped records of patient parameter values for storage in the EHR database. This data is often collected at sub-second granularity. If this data is then stored at even a minute-level granularity, the stored data can quickly become voluminous. Other examples of structured clinical event data include laboratory measurements, medications administered, treatments and procedures, and imaging results (including X-rays, CAT scans, MRI scans, and the like). In any of this structured clinical event data, noise and errors can be stored together with relevant information in the EHR database.

As described above, the EHR database also includes discharge summaries, which can include clinicians' notes regarding a patient's care. Given that discharge summaries attempt to distill a patient's care in a single record, it is more intuitive to mine discharge summaries to determine patient health conditions instead of mining the structured clinical event data. Further, the discharge summaries actually mention patient health conditions or outcomes, whereas the structured clinical event data does not. Thus, natural language processing (NLP) techniques have been applied to discharge summaries to identify patient outcomes and ultimately, billing codes for those outcomes.

Although these NLP techniques perform reasonably well, performance is limited by complex structure in the dictated sentences of discharge summaries. This complex structure includes short, telegraphic phrases that are ungrammatical in nature. Further, clinical narratives are rife with shorthand, including abbreviations, acronyms, and local dialectal shorthand phrases. These shorthand lexical units are often overloaded, such that the same set of letters has multiple meanings. In addition, misspellings abound in clinical texts, and the presence of special characters and noise introduced due to transcription make word tokenization difficult. These problems occur in addition to other problems common to extracting semantics from complex natural language sentences.

Despite widespread focus on data mining of discharge summaries to determine patient outcomes, systems and methods herein counterintuitively mine the structured clinical event data to determine patient outcomes. Advantageously, as will be described in detail herein, mining the structured clinical event data instead of or in addition to mining discharge summaries can increase the accuracy of patient outcome identification. In one embodiment, systems and methods described herein use sophisticated language models to extract outcomes from discharge summaries while also inferring outcomes from cues or hints contained in the structured clinical event data. For example, the clinical event data can include information regarding treatments and medications prescribed by clinicians to specifically manage patient complications; thus, presence or absence of relevant treatments in the clinical event data can provide independent indicators to disambiguate cases where current discharge-summary/NLP approaches fail. Similarly, clinical events such as a test being ordered or use of equipment as a measurement device (e.g., a ventilator) can also be analyzed to infer that specific complications exist.

More generally, embodiments of systems described herein do not need to rely on direct hits of keywords in a discharge summary to determine patient health conditions. Rather, these systems can infer patient health conditions or billing codes from data that does not mention patient health conditions directly. This inference can include deducing conclusions from facts that indicate that a patient likely had a particular health condition. If a certain medicine was given to a patient, for example, the system might infer that that this type of medicine would typically be used to treat a particular health condition, and that therefore the patient has that condition. The system can also make inferences based on multiple different data points. For example, a patient may have had both a certain medicine and a CAT scan, which together indicate that the patient was likely treated for a certain condition.

Automated extraction of patient outcomes from the rich data source of clinical event data can serve as a basis for medical billing and informatics, clinical trial recruitment, research, bio-surveillance, or other applications.

II. Example Medical Classification Systems

Figure 1B:
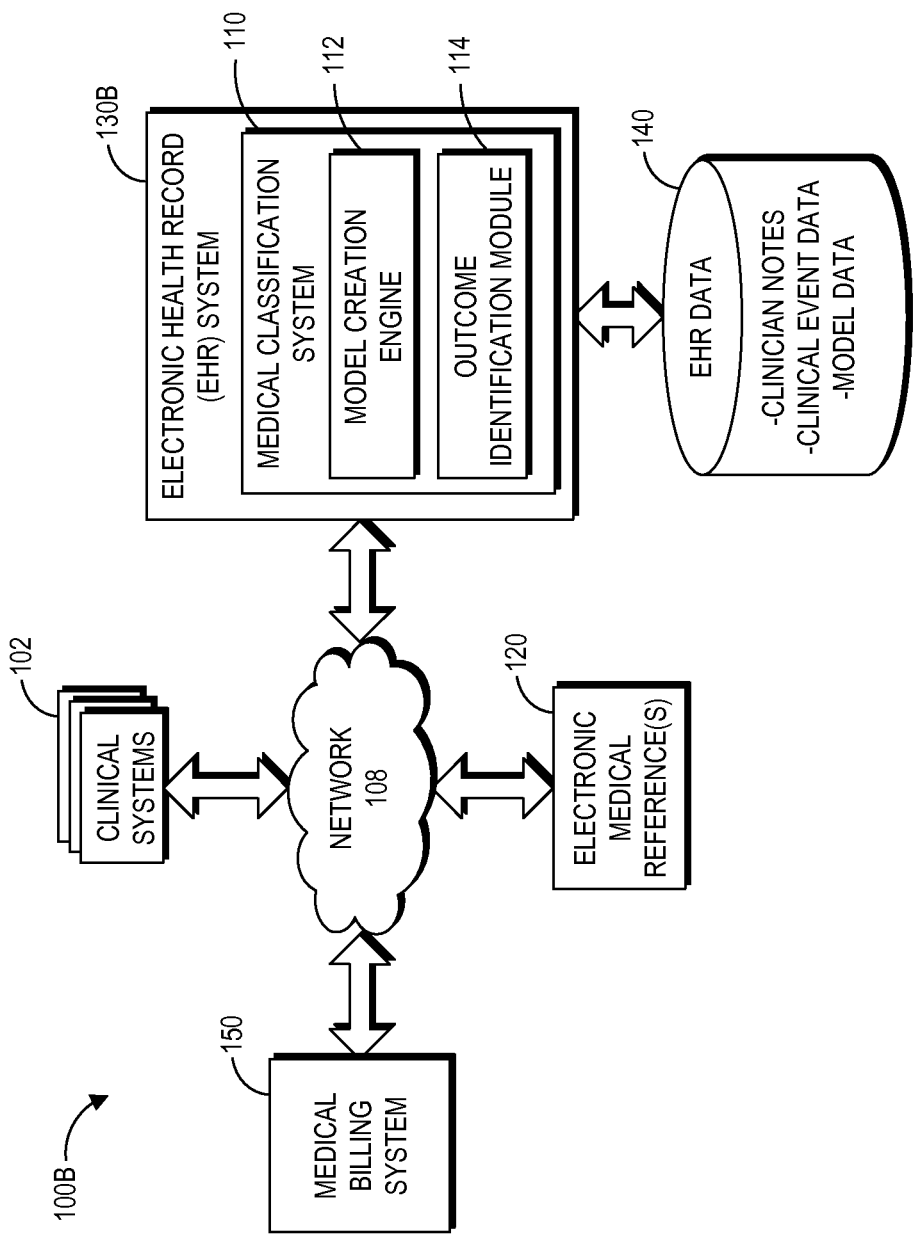
FIG. 1B illustrates another embodiment of a computing environment that can implement a medical classification system.

Features related to the analysis of structured clinical event data and discharge summaries will be described in the context of example medical classification systems shown in FIGS. 1A and 1B. In particular, FIG. 1A illustrates an embodiment of a computing environment 100A that can implement a medical classification system 110, and FIG. 1B illustrates another embodiment of a computing environment 100B that can implement the medical classification system 110. The computing environment of FIG. 1A depicts the medical classification system 110 as a separate system from an electronic health record (EHR) system 130A. In FIG. 1B, the medical classification system 110 is integrated in the health record system 130B. The computing environments 100A, 100B shown in FIGS. 1A and 1B can be implemented in any clinical facility, including a hospital, an outpatient care center, a lab, a doctor's office, skilled nursing and assisted living facilities, and the like, or in a data center separate from a clinical facility.

Referring specifically to FIG. 1A, the medical classification system 110 communicates with the EHR system 130A over a network 108, which can be a clinical facility LAN, a WAN, the Internet, combinations of the same, or the like. Also shown in communication with the network 108 are clinical systems 102 and an electronic medical reference 120 (or references). Further, in communication with the medical classification system 110 is a medical billing system 150. Each of these systems shown can be implemented using software and/or computer hardware (example hardware is described in greater detail below).

Referring specifically to FIG. 1B, the medical classification system 110 is installed directly in the EHR system 130B. Installing the medical classification system 110 directly in the EHR system 130B can provide the benefit of tight integration with the existing EHR system 130B. Thus, in the depicted embodiment, the medical classification system 110 does not need to communicate over a network to extract data from the EHR system 130B; rather, the medical classification system 110 has direct access to the data stored in the data repository 140. As shown, the data repository 140 can therefore also serve as a repository for storing model data (described below).

By way of overview, in either FIG. 1A or 1B, the medical classification system 110 can communicate with the EHR 130A to obtain discharge summary information and/or structured clinical event data for one or more patients. The medical classification system 110 can programmatically analyze this data to identify patient health conditions or outcomes. In one embodiment, the medical classification system 110 identifies billing codes based on the analyzed data. The medical classification system 110 can provide billing codes for each patient analyzed to the medical billing system 150, which can use the billing codes for managing patient billing. In addition, the outcomes identified by the medical classification system 110 can be used for other purposes, as described above. In other embodiments, the medical classification system 110 outputs billing codes but not directly to the medical billing system 150.

The EHR 130A can include software and systems to store and provide access to electronic medical records (EMR). In many systems, the terms "EHR" and "EMR" are used synonymously. Other terms commonly used to refer to the EHR 130A and its data include electronic patient records (EPR) and computerized patient records. More generally, it should be understood that in addition to having its ordinary meaning, the term "EHR," as used herein, can refer to any system or database that stores patient data. This patient data can include notes by clinicians (e.g., doctors, nurses, technicians, or other clinical staff) such as discharge summaries, and/or structured clinical event data.

Structured clinical event data is often provided to the EHR 130A via clinical systems 102 over the network 108. These clinical systems 102 can include bedside monitors or other medical devices that obtain physiological monitoring data from patients. The clinical systems 102 can also include user computing devices operated by clinicians for the purpose of entering a record of any of the following information, among others: medicines administered, lab reports including culture reports, radiology reports, and the like, treatments performed by clinicians or medical devices (such as ventilators), and so on. In one embodiment, the clinical systems 102 include hospital chart systems, nurses' stations, PDAs, smartphones, or other devices operated by clinicians, hospital kiosks, and the like. These clinical systems 102 may, but need not be, in the same location as the EHR system 130A.

The EHR system 130A receives clinical event data and clinician notes (including discharge summaries) from the clinical systems 102 and stores this data in an EHR data repository 140. The EHR data repository 140 can include one or more databases implemented in one or more physical computer storage devices. The EHR data repository 140 can include data structures, such as tables, that map patients to their respective clinical event data and clinician notes. The clinical event data can include a record of time-stamped events that occur with respect to a patient. For example, the clinical event data can be structured to include one or more regular fields of time-stamped data. Thus, the clinical event data can be more structured than the free-text of clinician notes. Simpler NLP techniques can be used to extract information from the clinical event data due to this structure, as the desired data is often in expected locations (such as predefined table columns). The following table illustrates an example of structured clinical event data obtained from the Neonatal Intensive Care Unit (NICU) at the Lucile Packard Children's Hospital of Stanford University (LPCH):

TABLE 1

| Structured Clinical Event Data PatientID - Time since birth - Name - Dosage - Units |
|---|
| 53004567 - 14.00:00:00 - Sodium Chloride 0.45% - 0.999001 - mL |
| 53004567 - 14.00:00:00 - heparin - 0.999001 - units |
| 53004567 - 14.00:00:00 - IVPARENT - 1.000000 - mL |
| 53004567 - 14.01:00:00 - fat emulsion, intravenous - 0.300000 - units |
| 53004567 - 14.01:00:00 - IVPARENT - 0.300000 - mL |
| 53004567 - 14.02:00:00 - fat emulsion, intravenous - 0.300000 - units |
| 53004567 - 14.02:00:00 - IVPARENT - 0.300000 - mL |
| 53004567 - 14.02:00:00 - furosemide - 0.600000 - mg |
| 53004567 - 14.03:00:00 - parenteral nutrition solution - 2.000000 - mL |
| 53004567 - 14.03:00:00 - IVPARENT - 2.000000 - mL |
| 53004567 - 14.03:00:00 - Sodium Chloride 0.45% - 0.999001 - mL |
| 53004567 - 14.03:00:00 - heparin - 0.999001 - units |
| 53004567 - 14.03:00:00 - IVPARENT - 1.000000 - mL |

Table 1 includes medication administration information. As can be seen in Table 1, the administration of medication is shown in highly structured form, with the patient ID, a time stamp since birth, the name of the drug, dosage, and units given listed for each administration. In contrast, the following excerpt of a discharge summary illustrates the unstructured nature of free-text clinician notes:

| Example Discharge Summary |
|---|
| ADMISSION DIAGNOSES: <cr>1.  A 31-6/7-week male infant, twin B.<cr>2. Prematurity.<cr>3    Possible   sepsis.<cr><cr>DISCHARGE DIAGNOSIS: <cr>1. A  day  of  life number  34,  ex-31-6/7-week male infant,  now  36-5/7-weeks<cr>postconceptual age.<cr>2. Mild indirect  hyperbilirubinemia. <cr>3.         Resolved    mild apnea   of    prematurity. <cr>4.        Mild physiologicanemia. <cr>5. Immature   retinae.<cr><cr>IDENTIFICATION: XXXX      XXXX XXXX is a  day  of  life number  34,  ex-31-6/7-week<cr>male infant who was admitted secondary to prematurity and possible sepsis. His<cr>hospital course has been fairly unremarkable.    He was advanced to  full  feeds.   He <cr>has  tolerated  this  well  and  has  bouts of intermittent mild,  indirect<cr>hyperbilirubinemia.     He  is now being discharged home with follow-up with Dr.   XXX<cr>XXXX at the Palo Alto Medical Foundation.<cr><cr>BIRTH HISTORY:  XXXX |

-continued

Example Discharge Summary

XXXX XXXX is a 1,640 gram product of a<cr>monochorionic-diamniotic concordant twin gestation pregnancy. He was born at<cr>Lucile Salter Packard Children's Hospital at 31-6/7-week gestation to a<cr>30-year-old, gravida 2, para 1-0-0-1 mother who received good prenatal care. <cr>Prenatal laboratories were as follows: Blood type B positive, antibody screen<cr>negative, hepatitis B surface antigen negative, rubella immune, RPR negative, <cr>gonorrhea and Chlamydia negative, HIV negative, and group B strep negative on <cr>XX/XX/XX. The mother had an initial Glucola screen Discharge Summary Excerpt The EHR 140 data repository can store a table that includes data such as that shown in Table 1, with a column for each of the columns shown. Thus, identifying and accessing this data using NLP techniques can be relatively straightforward. On the other hand, such a table merely includes a list of medications given and the relevant parameters of those medications and not the actual health conditions addressed by those medications. In contrast, the discharge summary excerpt shown explicitly mentions health conditions such as "mild indirect hyperbilirubinemia" and "immature retinae." The challenge of analyzing discharge summaries lies in identifying these health conditions from the difficult to extract, free-flowing, unstructured text. The challenge of analyzing structured clinical event data lies in inferring the health conditions from the relatively easy-to-extract, structured text. Advantageously, in several embodiments, the medical classification system 110 can analyze both types of data (or solely the clinical event data) to improve and enhance the extraction of health conditions or outcomes from the EHR 130A system.

The challenge of inferring health conditions from the clinical event data can be very great. This challenge is partially due to the sheer enormity of the data. For example, in the LCPH, a thousand unique laboratory tests are done in the NICU alone. Most of these tests have different noise characteristics that present additional challenges in interpreting the data. The data is also high-dimensional, as can be seen from the medications data shown in Table 1. Further, most parameters and treatments lack existing baselines and formal metrics against which they can be easily calibrated. Some or all of these problems (among others) can be overcome, at least in part, by sophisticated automated learning algorithms implemented by the medical classification system 110.

In the depicted embodiment, the medical classification system 110 includes a model creation engine 112 and an outcome identification module 114. By way of overview, the model creation engine 112 can create a medical classification model that can be used to analyze clinical features in the structured clinical event data. The model creation engine 112 can also analyze aspects of the clinician notes, including discharge summaries, to extract language features relevant to patient outcomes. The outcome identification module 114 can analyze clinical features in the structured clinical event data with respect to the model to identify patient outcomes, and ultimately billing codes. The outcome identification module 114 can also analyze language features together with, or independently from, the clinical features to identify patient outcomes.

The model creation engine 112 can use electronic and/or human input to create a model that extracts rules based on the clinical event data and/or clinician notes data. These rules can map clinical features from the clinical event data to outcomes and/or language features in the clinician notes to outcomes. Language features are described in more detail below. Clinical features can include structured information obtained from the clinical event data, some examples of which include medications, clinical events, culture reports, and radiology reports (see FIG. 2). Using a boosting technique or other techniques (such as NLP techniques), the model creation engine 112 can extract rules from a known ontology, such as the electronic medical reference(s) 120 (an online medical dictionary, encyclopedia, or the like). One specific example of an electronic medical reference 120 that can be used is the Unified Medical Language System (available at www.nlm.nih.gov/research/umls). For instance, the model creation engine 112 can automatically identify clinical features in the electronic medical reference(s) 120 that correspond to particular health conditions and create rules that map each feature to the identified condition. In another embodiment, the model creation engine 112 extracts candidate rules from the electronic medical reference 120, selects a subset of those rules, and then automatically weights those rules (see below). More generally, the model creation engine 112 can use any feature-pruning or feature selection algorithm to mine rules from the electronic medical reference(s) 120.

To illustrate, the model creation engine 112 can identify from an online medical reference 120 that the medication "Albuterol" is used to treat the condition "asthma." The model creation engine 112 can then store a rule in a model data repository 118 that maps the medication Albuterol to the condition asthma. This mapping can include storing the clinical features and health conditions in a data structure, such as a table. The rules created by the model creation engine 112 can be refined or added to by an expert, such as a clinician, in some embodiments. In other embodiments, a clinician provides the rules to the model creation engine 112 instead of the model creation engine 112 automatically obtaining the rules from the electronic medical reference(s) 120.

The model creation engine 112 can then assign weights to the rules automatically in a training process that uses actual clinical event data and known health outcomes. Each weight can reflect the degree to which a given clinical feature is indicative of a given outcome. In several embodiments, the weights are in the range of (0, 1], where 1 indicates a high degree of correlation between a feature and an outcome close to 0 indicates low correlation between a feature and an outcome (if the correlation is 0, the rule might not be stored). The weights can also have a range other than (0, 1]. Continuing with the Albuterol example, Albuterol is also used to treat bronchospasms due to other health conditions, such as Bronchitis. Thus, the expected weight for the rule that the administration of Albuterol indicates the presence of Asthma may be less than 1 because there is not a one-to-one correlation between Albuterol use and the presence of Asthma in a patient. While such a weight could be hand-tuned by an expert, hand-tuning a large data set like the EMR data repository 140 could be extremely time-intensive, less efficient, and potentially less accurate than using an automated training process. Example automated training processes are described in detail below with respect to FIG. 2.

The model creation engine 112 can store the rules, together with their weights, as a model in the model data repository 118. The model creation engine 112 can construct different models for different patient populations, such as a NICU population model, an ICU population model, a general monitoring floor (of a hospital) population model, population models based on age or gender or location, and so forth. Alternatively, the model creation engine 112 can construct a monolithic model that represents multiple (or all) patient populations.

In some embodiments, the model creation engine 112 is run once, when the medical classification system 110 is installed. In another embodiment, the model creation engine 112 is run once prior to installation of the medical classification system 110. Thus, the model data repository 118 can be supplied to a clinical facility with a pre-generated model based on data from a similar population to a population that will be analyzed using the medical classification system 110. The model creation engine 112 can therefore be a separate component of the medical classification system 110 in some embodiments, and not included in a clinical facility installation. In other embodiments, the model creation engine 112 can refine the model after the model is initially created, for example, by continually or periodically analyzing the patient data in the EHR data repository 140.

The outcome identification module 114 can apply the rules of the model to the patient data (including clinical event data and optionally clinician notes) to identify possible health conditions or outcomes. In one embodiment, the outcome identification module 114 subsequently maps each health condition to one or more billing codes. In another embodiment, the outcomes are the billing codes. Thus, the outcome identification module 114 can apply the rules to directly obtain billing codes.

It should be noted that, in either FIG. 1A or 1B, the medical classification system 110 can include software that executes on one or more computing devices, such as one or more physical server computers. In embodiments where the medical classification system 110 is implemented on multiple servers, these servers can be co-located or can be geographically separate (such as in separate data centers). In addition, the medical classification system 110 can be implemented in a cloud computing platform, such as may be available from Amazon Web Services™, the Windows Azure™ Platform, or the like. For instance, the medical classification system 110 can be implemented in one or more virtual machines that execute on one or more physical servers. More generally, the medical classification system 110 can be implemented as software-as-a-service (SaaS), using an application service provider model or the like.

It should also be noted that structured clinical event data can be voluminous in nature. Thus, it may not be possible for an individual to manually perform the analysis of structured clinical event data as described herein. For example, in some embodiments, structured clinical event data can include hundreds or thousands of entries of data for a single patient. Compound this data among many patients, and the task of identifying billing codes from structured clinical event data can quickly become impossible with the human mind or pencil and paper alone. In contrast, the systems described herein can, in certain embodiments, automatically analyze patient data, including structured clinical event data and/or clinician notes, much faster than a human could do, making such analysis feasible to do. As one example, a computer system implementing embodiments of the features described herein may be able to process records for a patient in real time, or can identify outcomes in less than a minute, or less than two minutes, or less than five minutes, or less than some other time.

In addition to the potential benefits of the medical classification system 110 in the medical billing context, the medical classification system 110 can provide benefits in other contexts. For instance, automated extraction of patient outcomes by the medical classification system 110 can serve as a basis for clinical trial recruitment, research, bio-surveillance, or other applications. Patient outcome extraction can benefit clinical trial recruitment in some embodiments by enabling researchers to identify subjects who are known to have a particular outcome (e.g., based on analysis by the medical classification system 110). Outcome extraction can also provide additional avenues for research of long term and short term health complications and can allow researchers to compare a gold standard of outcome identification (e.g., provided by the medical classification system 110) to predicted outcomes. Outcome extraction provided by medical classification system 110 can also have applications in bio-surveillance. For instance, an organization like the Centers for Disease Control and Prevention (CDC) can monitor extracted outcomes to identify whether a certain strain of disease is more prevalent than normal. The medical classification system 110 can also have applications in other areas than those mentioned.

In addition, it should be noted that the medical classification system 110 can improve patient care by alleviating clinicians' billing burdens. For instance, with the automated billing code identification provided in some embodiments by the medical classification system 110, doctors can focus more on what care to give patients rather than what codes to bill to receive reimbursement.

III. Example Medical Classification Processes

Figure 2A:
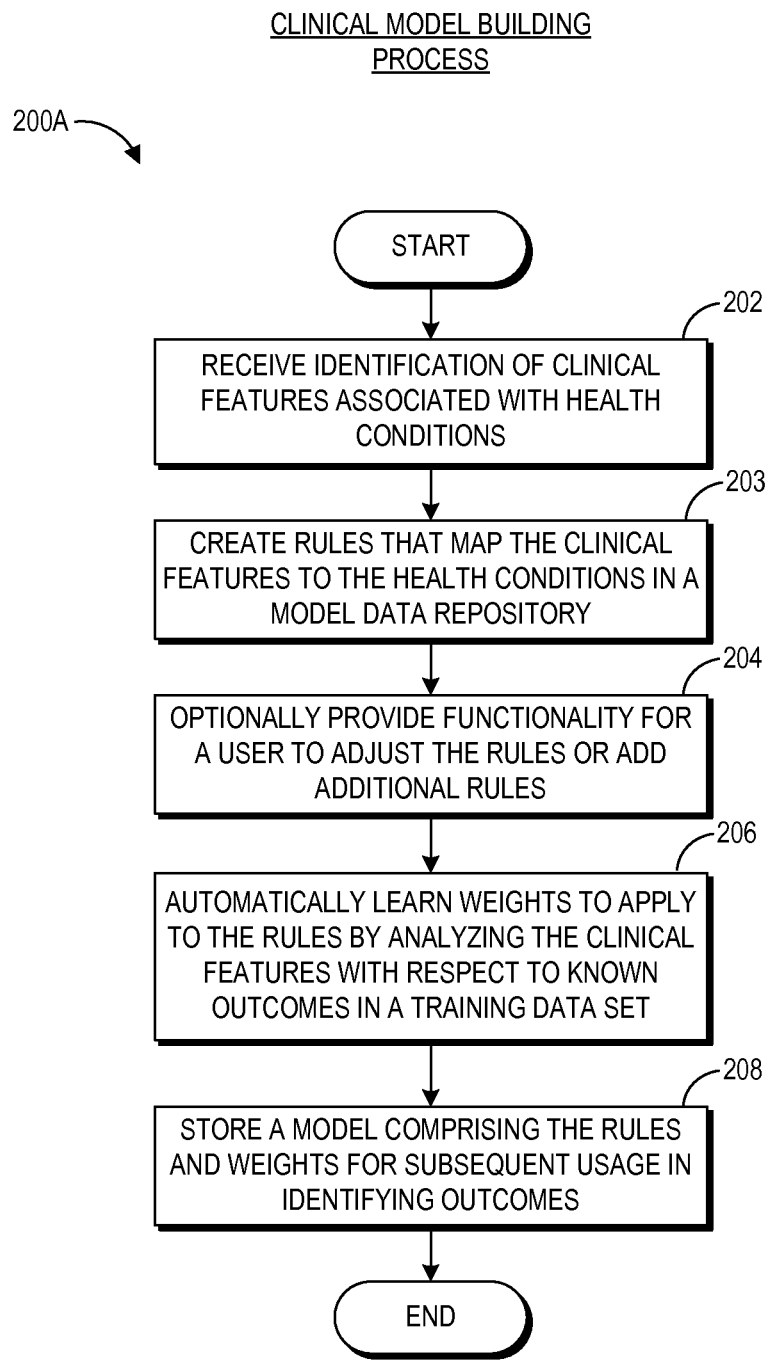
FIGS. 2A and 2B illustrate embodiments of model building processes that can be implemented at least in part by the medical classification system of FIG. 1A or 1B.
Figure 2B:
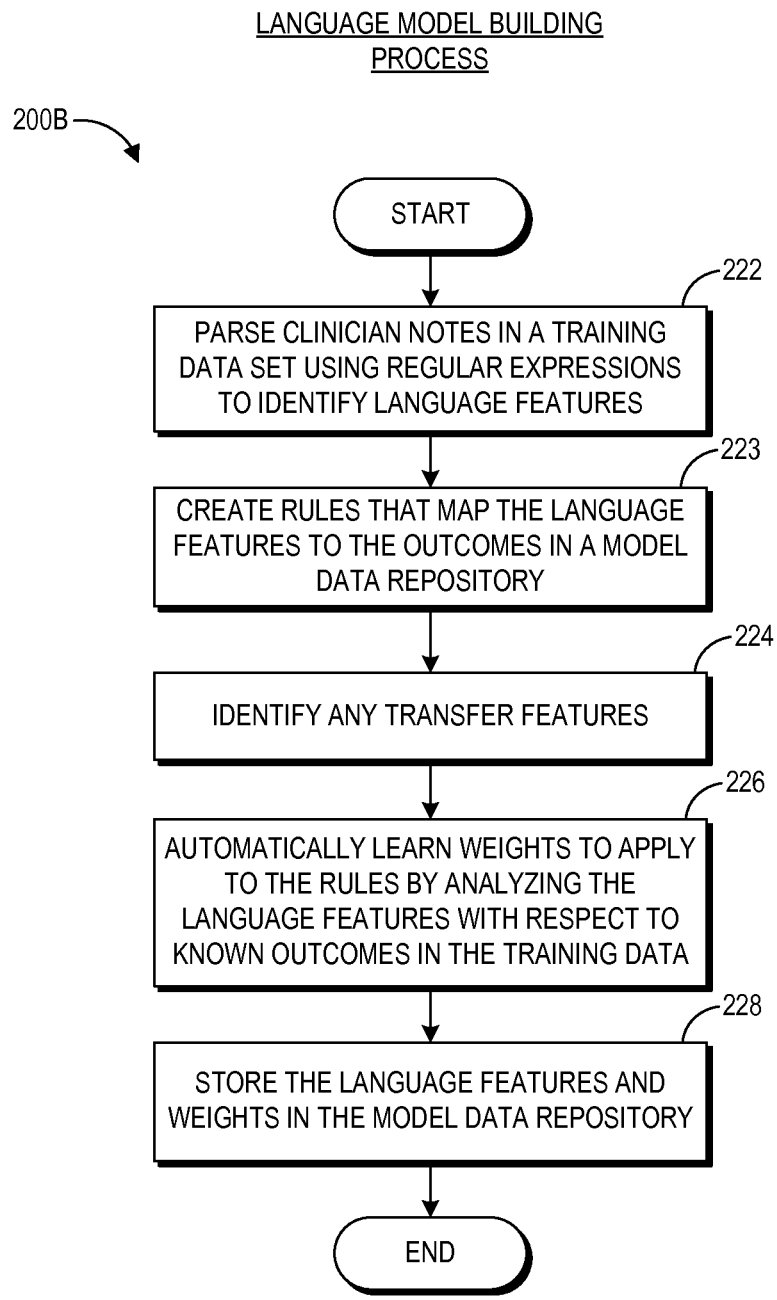
Figure 3:
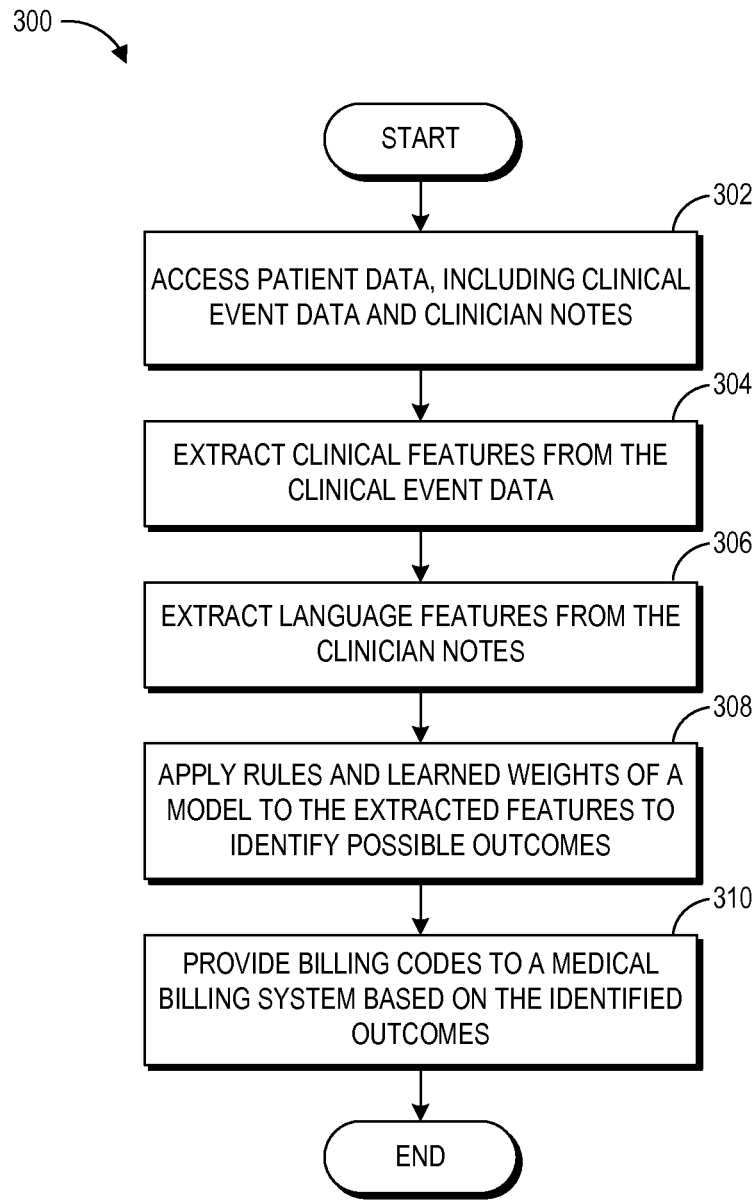
FIG. 3 illustrates an embodiment of an outcome identification process that can also be implemented by the medical classification system of FIG. 1A or 1B.

FIGS. 2A, 2B, and 3 illustrate example processes 200A, 200B, 300 that can be implemented by the medical classification system 110 to implement some or all of the features described above. For purposes of illustration, the process 200A, 200B of FIGS. 2A and 2B are described as being implemented by the model creation engine 112 of FIG. 1. Likewise, the process 300 of FIG. 3 is described as being implemented by the outcome identification module 114 of FIG. 1. However, the processes 200A, 200B, 300 are not limited to the specific systems and components described herein, but can also be implemented by other systems than those described.

Referring specifically to FIG. 2A, an embodiment of a model building process 200A is shown. This model building process 200A can build a clinical model from structured clinical event data. The process 200A begins at block 202, where the model creation module 112 receives an identification of clinical features associated with health conditions. In some embodiments, receiving this identification of clinical features includes programmatically identifying the clinical features and associated health conditions from the electronic medical reference(s) 120. The model creation module 112 can use NLP techniques to extract these rules from the electronic medical reference(s) 120. In other embodiments, the clinical features are identified by an expert, such as a clinician, instead of or in addition to an automated identification.

At block 203, the mode creation engine 112 creates rules that map the clinical features to the health conditions in a model data repository. These clinical features and rules related to such features can fall into various categories. Examples of clinical feature categories including medications, clinical events, culture reports, and radiology reports. In more detail, these clinical features categories can include any subset of the following, among others:

Medications (M): The EHR 130 can store the medication name, dosage, along with the time at which the medication was administered as structured events. The model creation engine 112 can extract rules of the form (medication name(s), minimum length of prescription) for some or all relevant complications to a patient population. In one embodiment, such a rule is activated if a medication in the rule is administered to a patient for at least the minimum time.

Clinical Events (E): For various clinical events associated with complications, the model creation engine 112 can extract rules of the form (event name, minimum event duration, threshold event value). Events can include therapies (for example, infants with respiratory distress syndrome are often on oxygen therapy, which can be represented as (oxygen therapy, N days, N/A)) as well as lab measurements (for example, extended increase in creatinine measurements is indicative of a renal malfunction in infants). The model creation engine can model these rules as binary features, such that the existence of the feature is indicative of the health condition. Although these rules are modeled as binary features in some embodiments, weights can be applied to any of the rules described herein.

Rules related to clinical events can map discrete events to an outcome and/or can map a sequence or pattern of clinical events to an outcome. An example of a discrete event might be a single administration of a therapy. A sequence of events might include multiple therapy sessions over time. Different types of clinical events can occur in a sequence that may be indicative of a given outcome. More generally, sequences of clinical event data can be constructed of one or more different types of clinical event data. For example, the model creation engine 112 can extract rules that relate the following example sequence of events to an outcome: a time interval between obtaining a particular test (e.g., lab test), receiving the result, and the response in terms of medication given or the next clinical event (such as a therapy given). The events in a sequence can be time-ordered but need not be. The time information in some sequences can be relevant to a given outcome. For instance, medication administered within a short time after receiving a culture report might be indicative of a treatment of a disease related to the results in the culture report.

Culture Reports (C): Culture status is relevant to various health conditions. A vast majority of culture reports have a section that summarizes the result of the culture, where "No growth" is mentioned unless any microbial (bacterial or virus) growth is observed. The presence of growth may be a result of a contaminant, which is further discussed in the unstructured text section of the report. The result of each report can be encoded as a binary rule. The count over some or all reports for any given patient can be modeled as a multinomial feature.

Radiology Reports (R): Features in radiology reports can also be extracted and mapped to outcomes as rules. These features can relate to aspects of x-ray reports, CAT scans, MRI scans, and the like.

At block 204, the model creation engine 112 optionally provides functionality for a user to adjust the rules or add additional rules. The rules generated automatically in blocks 202 and 203 may benefit from attention by an expert to confirm that the machine-learned rules are valid. Further, it can be helpful for an expert to add any additional rules that may not be extractable by accessing electronic medical references. In other embodiments, the model creation engine 112 further provides functionality (such as a user interface or scripting interface) for adding initial weights or adjusting weights to be applied to the rules (see block 206). For instance, the model creation engine 112 may allow the clinician to specify initial weights, which the engine 112 may refine programmatically, or to adjust weights that the engine 112 learned programmatically. However, in some embodiments, the features associated with block 204 may be omitted.

At block 206, the model creation engine 112 automatically learns weights to apply to the rules by analyzing the clinical features with respect to known outcomes in a training data set. The model creation engine 112 can store a model comprising the rules and weights for subsequent usage in identifying outcomes at block 208. The training data set can include data of a population of interest. For example, the training data set can include existing data in the EHR data repository 140 for a given patient population. In one embodiment, the training data set is selected from patient records that already have outcomes assigned to them, such as billing codes or identified health conditions. Alternatively, a clinician can first identify the outcomes associated with the patients in the training data set.

With the outcomes known or otherwise pre-identified, the clinical features can then be analyzed and compared with the known outcomes to assign weights to the clinical features. This analysis can include searching the training data set to identify the clinical features associated with each patient and then using a learning algorithm to assign to each feature weights that represent that feature's contribution to the outcome. Many different types of learning algorithms can be used. Some examples of learning algorithms include algorithms based on logistic regression, maximum likelihood estimation (MLE) techniques, maximum a posteriori estimation (MAP) techniques, neural networks, support vector machines, and boosting, combinations of the same, or the like. In one embodiment, the learning algorithm is any supervised machine learning algorithm, such that the algorithm generates a function that maps inputs (the weights of clinical features) to desired outputs (the outcomes; also referred to herein as labels). In other embodiments, semi-supervised learning algorithms or manual procedures can be used to train or adjust the rule weights.

The following example learning algorithm is provided as a non-limiting illustration of techniques that can be used to learn the rule weights. This algorithm implements a penalized logistic regression model that combines some or all clinical features. While a broad set of classifiers can be deployed, penalized logistic regression can perform well in the low data regime, such as may be found in some training data sets. With a small number of data samples, a penalization scheme can force the rule weights to be smaller so that the weights do not exaggerate the importance of individual features. For example, in some embodiments, the weights for the model are learned in this example using maximum likelihood estimation (MLE) regularized with ridge regression, which trades off fit to data with model complexity, as measured by the sum of the learned weights. In other embodiments, where larger training data sets may be used, the learning algorithm can be implemented without a penalization scheme.

For instance, a training objective can be optimized or attempted to be optimized using the following expression or the like:

$$\operatorname{argmax}_{\vec{w}} \sum_{d=1}^{D} \sum_{i=1:N} \left[ -y_i^d \vec{w}^T \left( \vec{f}_i; \vec{s}^d \right) + \ln\left(1 + \exp\left( \vec{w}^T \left( \vec{f}_i; \vec{s}^d \right) \right)\right) \right] + \frac{1}{2\sigma^2} \|\vec{w}\|^2 \quad (1)$$

where N is the number of training examples, d indexes each of the outcomes (e.g., complications or billing codes), $f_i$ are the clinical features (e.g., occurrence counts of each clinical feature in the clinical event data) and $y_i \in \{0,1\}$ is the label (outcome) of the ith example ("1" indicating the outcome occurred and "0" indicating that it did not occur), $s^d$ selects the features in the vector $f_i$ relevant to each outcome ($s^d=1$ if the feature is extracted as being relevant to outcome d and 0 otherwise), w is a vector of weights to be learned, and σ controls the magnitude of a ridge penalty.

The expression "argmax$_w$" indicates that the weight vector w is to be selected so as to maximize the expression to the right of "argmax$_w$." The expression can be deterministically solved by taking the gradient of the expression, setting this gradient equal to zero, and solving for w. Numerical approximation techniques may also be used to solve this equation. For example, the expression can be maximized by making an initial guess of the weights w and iteratively testing different values of the weights to maximize the expression.

In FIG. 2B, another embodiment of a model building process 200B is shown. This model building process 200B can build a language model from clinician notes (such as discharge summaries), which may be used separately from or combined with the clinical model described with respect to FIG. 2A. Advantageously, in some embodiments, the model building process 200B creates a rule-based model based on language features, which can have greater accuracy than traditional NLP techniques.

The process 200B begins at block 222, where the model creation module 112 parses clinician notes in a training data set using regular expressions to identify language features. Like the clinical features described above, the language features obtained at block 222 can be indicative of outcomes, such as health conditions or billing codes. The model creation engine 112 can look for specific language features, some examples of which are described below. At block 223, the model creation engine 112 creates rules that map the language features to the outcomes in a model data repository. In one embodiment, a clinician or other expert labels the language features specifically with outcomes, and the model creation engine 112 stores these labels together with the language features in the model data repository.

In some embodiments, the language features identified by the model creation engine 112 can fall under categories of typical linguistic contexts in which patient disease outcomes are mentioned. The types of contexts which suggest a positive, negative, or uncertain result can be fairly consistent within the domain of medical records, making it possible to engineer regular expressions that capture and categorize a majority of these mentions correctly. Four basic types of language feature categories can be analyzed by the model creation engine 112, among others:

Disease Mentions: In addition to health condition/complication/disease names, this category can include patterns to capture abbreviations (e.g., UTI and NEC), alternate spellings (e.g., haemorrhage and hemorrhage), complication subclasses (e.g., germinal matrix hemorrhage and intracranial hemorrhage for IVH), and synonyms (e.g., cardiac arrest for arrhythmia). Expert opinion can be used to increase feature coverage. Alternatively, the model creation engine 112 can query the electronic medical reference 120, such as the Unified Medical Language System (UMLS—www.nlm.nih.gov/research/umls) to increase feature coverage.

Negations: The model creation engine 112 can use a NegEx-inspired strategy to identify both sentential and noun-phrase negations that indicate a negative result pertaining to one of the above disease name mentions. The NegEx functionality is described at http://code.google.com/p/negex/, the contents of the entire site of which are hereby incorporated by reference in their entirety. General patterns such as no|never MENTION and (no|without) evidence of MENTION can be used across some or all disease types, but disease specific negation patterns are also allowed where appropriate, for example, r/o SEPSIS (rule out sepsis).

Uncertainty Modifiers: The model creation engine 112 can identify uncertain contexts from patterns of similar construction to the negation patterns but include templates such as (possible|suspected) MENTION and history of MENTION. In doing so, the model creation engine 112 can identify regions of uncertainty in order to avoid overvaluing many disease name mentions. Disease-specific uncertainty patterns may also be used to recognize information that is most likely unrelated to patient outcome, for example, family death or pregnancy-related UTI.

Correlated Words and Phrases: This category of language features can come from reviewing with experts words that showed high correlation with the outcome label, or from an automated analysis of the electronic medical reference(s) 120. Similar to the process of automatically extracting symptoms, medications, and related procedures from the description of previously billed codes, the data can be reviewed with a clinician and pattern matches can be determined for names and abbreviations of relevant antibiotics, treatments (e.g., antibiotics discontinued indicates sepsis ruled out), symptoms (PAC indicates arrhythmia) and tests (head ultrasound).

In several embodiments, the model creation engine 112 also identifies language transfer features at block 224. These language transfer features can represent patterns that repeat across multiple complications or outcomes, allowing the model creation engine 112 to generalize from one label to another without having seen mentions of a certain feature in the training data. For example, the text "without sepsis" and "without pneumonia" both suggest the mention of the disease in a negated context. With a transfer feature "without (disease name)," a negative weight learned from sepsis can be applied in the context of pneumonia. Other examples of transfer features can include "(disease name) ruled out" and "concern for (disease name)."

Another example of a transfer feature is "positive mention (infrequent disease name)," which encodes sharing amongst infrequently occurring complications. Complications like sepsis that are rampant in the population are discussed in almost every discharge summary and are ruled out using tests. Infrequent complications are only discussed when the patients show complication-specific symptoms and thus, their mention alone is strongly correlated with having the complication. The model creation engine 112 can encode each feature by a set of regular expressions that capture varying mentions in the data. Weight sharing can also be introduced for clinical features that are common to multiple complications (e.g., a positive blood culture is a diagnostic test used for both BAC and BCS).

At block 226, the model creation engine 112 automatically learns weights to apply to the rules by analyzing the language features with respect to known outcomes in the training data. In doing so, the model creation engine 112 can use any of the machine learning algorithms described above with respect to FIG. 2A. For example, the model creation engine 112 can implement logistic regression using MLE or some other technique. Advantageously, in some embodiments, the language features and the clinical features can be learned together in the same MLE optimization problem.

In another embodiment, to learn the language feature weights, in the training objective for each example, some or all the disease specific and transfer features that are activated can be combined by the model creation engine 112. Thus, the inclusion of both transfer and disease specific features with a ridge penalty can allow the model to learn specificity when there are large number of examples and generality for rare outcomes. In more detail, weight sharing can be implemented by the model creation engine 112 in one embodiment by modifying the learning objective of equation (1) as follows:

$$\operatorname{argmax}_{\vec{w}} \sum_{d=1}^{D} \sum_{i=1:N} \left[ -y_i^d \vec{w}^{d^T} \left( \vec{h_i} \vec{s}^d \right) + \ln \left( 1 + \exp \left( \vec{w}^{d^T} \left( \vec{h_i} \vec{s}^d \right) \right) \right) \right] + \quad (2)$$

$$\frac{1}{2\sigma^2} \|\vec{w_l}\|^2 + \frac{1}{2\sigma^2} |\vec{w_g}|^2$$

where $\vec{w}=[w_l, w_g]$ and $\vec{h}=[f_l; f_l]$. The new feature vector $\vec{h}_i$ can be formed by concatenating the matched language features twice. The vector $s^d$ can select indices in $\vec{h}_i$ for features relevant to sepsis (or another outcome) but not relevant to any other complication. Thus, for example, the element corresponding to the "rule out sepsis" feature in $s^d$ may be 0 in all diseases except sepsis. The weights w, are outcome-specific feature weights. The weights $w_g$ are global weights for features that are shared between complications. Thus, the prediction for each data instance can contain a contribution from the outcome-specific weights and the global weights.

At block 228, the model creation engine 112 stores the language features and weights in the model data repository 118. In doing so, the model creation engine 112 can create a separate language model from the clinical model created using the process 200A. Alternatively, the model creation engine 112 can combine the language features and weights with the clinical features and weights in a single, unified model. In doing so, the model creation engine 112 may create the weights for the language features and clinical features at the same time, using either equation (1) or (2) (or some other learning technique).

Moreover, at least some language features may be extracted from the clinical event data, or at least some clinical features may be extracted from the clinician notes data. For instance, culture reports and radiology reports can include text that may benefit from the language feature extraction analysis described herein. In particular, for a radiology report, the model creation engine 112 can extract sections in decreasing order of relevance until a non-empty section is available. The model creation engine 112 can parse the section for indications of the complication or symptom mentioned in a positive, negated or uncertain context using the language rules described above. Similarly, clinician notes can include mentions of medications, clinical events, culture information, or radiology information. The model creation engine 112 can extract this information as clinical features in some embodiments.

Although the clinical model building process 200A is illustrated separately from the language model building process 200B, at least part of these processes 200A, 200B can be implemented together in some embodiments. For instance, the learning of weights performed in block 206 of the process 200A and block 226 of the process 200B can be performed together. In other words, the weights for both clinical features and language features can be trained together.

FIG. 3 illustrates an embodiment of an outcome identification process 300 that can also be implemented by the medical classification system 110. The outcome identification process 300 can identify outcomes, including billing codes and/or health conditions of a patient. The outcome identification module 114 can implement the process 300. In one embodiment, the process 300 is performed subsequent to the process 200A and/or 200B being performed. In other words, outcome determination can be performed on a live patient data set after the model has been generated using a training patient data set.

The process 300 begins at block 302, where the outcome identification module 114 accesses patient data from the EMR data repository 140, including clinical event data and clinician notes. The outcome identification module 114 can access a single patient's data at a time or data from multiple patients at the same time. At block 304, the outcome identification module 114 extracts clinical features from the clinical event data, and at block 304, extracts language features from the clinician notes. The outcome identification module 114 can extract predetermined clinical and language features that corresponds with the clinical and language features stored in the model data repository 118.

Extracting these features can include determining a count of how often the features occurred. For instance, a clinical event such as actuation of a ventilator (or other medical device) may have been occurred several times during treatment of a patient. The outcome identification module 114 can count the number of times the ventilator was actuated and store this count in association with the clinical event. In the language context, a count of a number of disease mentions in clinician notes may be stored as well. For some clinical or language features, a higher count can be more indicative of an outcome, while a lower count can be more indicative of an outcome for other features. In one embodiment, the outcome identification module 114 stores a negative or inverse count value for features having an inverse correlation between count and outcome (e.g., low outcome indicates high likelihood of outcome and vice versa). These counts will be used to extract outcomes, as will be described shortly.

In some patient data, unexpected clinical or language features that have not be trained may arise. These features can be extracted and saved for subsequent incorporation into the model. For instance, if a new feature is identified and the patient is subsequently identified as having one or more outcomes, the model creation engine 112 can create a rule that associates the new feature with the one or more outcomes. The model creation engine 112 can then re-run the machine learning algorithm(s) to assign a weight to the new feature. Thus, in some embodiments, the model creation engine 112 can run continuously or periodically, as a background process or the like, refining the model(s). In another embodiment, the model creation engine 112 can output the new feature in a user interface or message (such as an email) to a clinician to request a weight to be manually assigned. In other embodiments, these new features can also be ignored.

Referring again to FIG. 3, at block 308, the outcome identification module 114 applies the rules and learned weights of a model to the extracted features to identify possible outcomes. Different algorithms may be used to accomplish this application of rules and weights. One algorithm that may be used is logistic regression, which corresponds to the logistic regression training described above with respect to FIGS. 2A and 2B. In logistic regression, an equation such as the following (or variants thereof) may be used to derive a probability value from features and weights:

$$p(z) = \frac{e^z}{e^z + 1} \quad (3)$$

where p(z) is a probability value mapped to the range [0, 1], e is Euler's number, and z is a value derived from the following expression:

$$z = w_0 + \vec{w_i}^T \vec{f_i} \quad (4)$$

In equation (4), $w_i$ and $f_i$ are the vectors described above with respect to equation (1) and/or (2), and $w_0$ is an intercept weight. In particular, in one embodiment, $f_i$ can represent the count of the $i^{th}$ feature.

Equation (4) can be rewritten using summation notation to reflect the linear combination of weights and feature counts in equation (4):

$$z = w_0 + \sum_j w_j f_j \quad (5)$$

As can be seen from equation (5), the value of z is greater when the feature count $f_i$ is greater or when the weights $w_i$ are greater. Plugging a greater value of z into equation 93) results in a higher probability p(z), and vice versa.

In certain embodiments, the outcome identification module 114 can calculate z and p(z) for each potential outcome for each patient. If there are 100 potential outcomes, for instance, the outcome identification module 114 can calculate z and p(z) 100 times for each patient. Some of the resulting probabilities p(z) may be higher than a threshold, in which case the outcome associated with those probabilities may be considered to have occurred. As a simplification to reduce processing resources, in some embodiments the outcome identification module 114 does not calculate a probability value for each outcome, but only for outcomes that have any features that are relevant to a given outcome.

The threshold selected for the probability value(s) p(z) can depend on any of a variety of factors. In one embodiment, the threshold can depend on a desired specificity and/or sensitivity. For example, a lower threshold can be selected to err on the side of capturing as many billing codes as possible (and thereby including potentially more false positives). A higher threshold can be selected to err on the side of capturing fewer false positives. In one implementation, the threshold can be set at 0.5 (or about 0.5) to achieve a balance between capturing more billing codes and accurate outcome identification.

At block 310, the outcome identification module 114 provides billing codes to the medical billing system 150 based on the identified outcomes. In one embodiment, the outcome identification module 114 first identifies health conditions and then looks these health conditions up in a lookup table or the like to identify the corresponding billing codes. In another embodiment, the outcome identification module 114 directly detects billing codes as the outcomes at block 308. Whether the outcome identification module 114 first detects health conditions or directly detects billing codes can depend on how the model is created by the model creation engine 112, as described above.

In alternative embodiments, the outcome identification module 114 can apply the process 300 separately for clinical events and for language events. The outcome identification module 114 may therefore obtain two probability values for some or all outcomes for a given patient. The outcome identification module 114 can then combine these two probability values. In one embodiment, this combination is performed as a linear combination of the two probability values, with a different weight assigned to probabilities from the clinical event data than probabilities derived from the clinician notes data. The probabilities may be weighted based on the particular outcome. For instance, some outcomes may be easier to detect from clinical event data, and others from clinician notes. The probabilities may be assigned accordingly to reflect these detectabilities, for example, with the clinical event data probability being weighted higher than the clinician notes probability if an outcome is better determined from a clinical event than clinician notes, and vice versa.

IV. Example Implementation and Results

Experiments were conducted using an embodiment of the model classification system 110 on the records of 275 premature infants born or transferred within the first week of life to the Stanford Lucile Packard Children Hospital's Neonatal Intensive Care Unit (NICU) after March 2008 and discharged before October 2009. Discharge summaries were extracted as well as laboratory reports of urine (188 reports) and blood cultures (590), radiology reports of ECHO (387) and head ultrasounds (534), medication events, and clinical events such as ventilator settings and tube placements. This study was approved under a Stanford IRB protocol.

A goal of using the medical classification system 110 was to identify, for each infant, any complications that occurred during their length of stay in the hospital. Administrative data such as ICD9 codes are known to have poor granularity and accuracy for identifying patient outcomes. To remedy this, two expert neonatologists formulated a list of major complications/outcomes observed in the NICU as shown in a table 400 of FIG. 4.

In the table 400, complications are listed in order of decreasing frequency in the data set collected. Clinical features were extracted from medications (M), clinical events (E), culture reports (C) and radiology reports (R), using at least some of the techniques described above. Overall, 33 clinical features were extracted. The patient data was annotated for these and any additional unlisted complications and subsequently reviewed by a team of three nurses and a physician. Overall, there were 628 unique complication-patient pairs marked as positive and 4872 complication-patient pairs marked as negative.

Results

Precision, recall, and F1 for each condition were computed, and then overall precision, recall, and F1 using micro-averaging were computed. Results reported were based on average test performance over 100 trials of randomized 70/30 train/test split (training on 70% of the data and testing on the remaining 30% of the data). A train/test split need not be used in all embodiments. Significance values are computed using the bootstrap method on the 100 trials.

Language Model

In one embodiment, a total of 285 language features were extracted. An aim of the experiments in developing the language model (LM) was to maximize its performance, so as to best evaluate the incremental contribution obtained from the clinical features. Thus, the LM development was done on the entire dataset using random 70/30 train/test splits. The cross-validation parameter σ (see equations (1) and (2)) was set to 0.8 to optimize test performance of the LM in the hold-out set, and not subsequently adjusted for the inclusion of the clinical features.

Figure 5:
FIG. 5 illustrates an example table that compares performance by embodiments of the medical classification system and another medical classification system.

Several approaches for combining the language features were considered so as to derive a strong baseline, as shown in a table 500 of FIG. 5. Other experimentation explored prefixed weighting schemes. A hand-tuned model was initially derived for the language features as follows: for a given patient-complication pair, sentences from the discharge summary that matched language features for that complication were extracted. Each sentence was allowed at most one vote; a "Yes" vote was assigned if only disease mentions without negations or uncertainty matched the sentence or a "No" vote if any negated mentions of the disease matched. To combine votes, a model that counted "No" votes twice as much as "Yes" votes gave the best results. DLM, deterministic language model (see FIG. 5), shows the performance of this fixed weighting scheme model. LLM, learned language model (see FIG. 5), shows performance of the model with weights learned assuming a bag of all matched features using the learning technique described earlier. Contributions of component feature classes to the baseline are also shown by adding them incrementally. LLM (with all language features) are used with F1 of 84.7 as the baseline for comparison with the EHR model (described below).

Integrated EHR Model

The EHR model generated in the experiments conducted contained the language features as well as the clinical features. Unlike the language model, the clinical features did not have an iterative feature development phase and were determined a priori using expert medical knowledge. (As discussed above, these features can alternatively be determined automatically using the electronic medical reference 120.) The model weights were trained using a bag of words assumption with weight sharing for the transfer features as detailed earlier. In a table 600 of FIG. 6, test performance of the EHR model is reported against a currently-available NLP language model. For visual clarity, the winning model based on F1 score is bolded for each complication.

Overall, the EHR model with average F1 score of 88.3 performs significantly (p-value=0.007) better than the language model. Additionally, the complications for which the EHR model does not outperform are those for which there were no clinical features included. In table 600 of FIG. 6, for each complication, clinical features were extracted from only one or two sources.

A post-hoc analysis of the results was done to understand the performance of the augmented EHR model. Three distinct sources of error were identified: (1) medical ambiguities, (2) feature error, i.e., failure of a language or clinical feature match on a specific instance, and (3) data extraction. Each of these errors can be improved upon by embodiments of the medical classification system 110.

A significant source of error within the dataset is inherent ambiguity in the process of medical diagnosis. Beyond cases that are simply complex to code, there are patients for which even medical experts disagree about the underlying diagnosis. This is especially true in the patient population used in evaluating embodiments of the medical classification system 110, who tend to have a multitude of secondary and tertiary complications stemming from their initial underlying condition. The highest achievable F1 score in the data with these examples included as errors is 96.3.

Feature errors in the language model (LM) can arise when context patterns fail to match because a lexical cue is separated from the disease mention by too much intervening text, but this turned out to be a relatively rare occurrence in the dataset. There were just four instances of error where syntactic parsing could have identified a modifier that was missed by regular expressions. A second type of language error, which occurs mainly with the most frequent complications of the presently used data set, SEPSIS and RDS, are spans that contain atypical contexts and/or require inference. In the sentence, "The workup was entirely negative and antibiotics were discontinued in approximately four days", there is no explicit mention of the complication, it can inferred that the patient most likely underwent a workup for sepsis. The addition of a 'Correlated Words' rule set helps mitigate these errors. In this case, for example, the rule antibiotics discontinued after X hrs/days correctly matched. In the full model, there were five errors of this type for RDS, one for SEPSIS, and one for PDA. The final type of feature error in the LM model is the most common, with at least ten instances in the complete dataset. It results when multiple mentions of a disease occur in conflicting contexts throughout the document or even within a single sentence. Temporal event resolution might improve performance in such cases.

Feature errors can also arise in clinical features, although less frequently due to the simplicity of their extraction. Such errors do occur mainly because combinations not covered by the feature set were administered. For example, cefotaxime or vancomycin are administered for at least four days when a patient has sepsis. However, some patients were switched from one to the other midway through their course, a feature not covered by the initial set.

A final source of error was due to errors in the data extraction software that was used, which is still in the first cycle of development. For more than 10 patients, subsets of their clinical records such as ultrasound reports, culture reports or clinical events were missing in the extracted dataset. Furthermore, for textual reports, occasionally missing word boundaries resulted in feature match errors.

It should be noted that in various other embodiments of the medical classification system 110, some or all of these errors can be eliminated.

V. Additional Embodiments

Embodiments of the systems and methods described herein can provide many advantages. For example, the medical classification system 110 can provide benefits for patients, clinicians, and/or health insurance providers such as HMOs or PPOs, or even the government (as a health insurance provider).

Some advantages that the medical classification system 110 can provide to patients include reducing the number of errors that occur in patient bills, and particularly, overbilling. Because the medical classification system 110 can more accurately detect or infer patient outcomes, the medical classification system 110 can provide more accurate billing codes. As a result, accidental or fraudulent overbilling can be reduced. In addition, mistaken codes can result in denied benefits; thus, reducing the number of mistaken codes can increase the chances that a patient's insurance benefits will cover the services billed.

Further, in one embodiment, the outcome identification module 114 of the medical classification system 110 includes a translator component that can translate patient outcomes to plainer English (or other language), so as to enable patients to better understand their hospital bills. Thus, for example, if a patient's health condition is a "neurological condition causing constriction of the vasculature," the outcome identification module 114 can identify this condition as a "migraine" for billing purposes. The patient's bill could be generated to include both the technical name of the health condition and the colloquial name ("migraine"), which may be depicted in parentheses. In one embodiment, the model creation engine 112 maps clinical and/or language features directly to colloquial or common names for health conditions, in addition to or instead of technical names or billing codes. Moreover, if medical bills are easier to read, it can be easier for patients and clinicians to prevent identity theft, where others use a patient's medical insurance wrongfully. The plain-language translations of medical services can help patients or clinicians instantly identify that a procedure was wrongfully provided, indicating possible identity theft or other fraudulent activity. Similarly, insurers can benefit from plain-language translations to thereby detect potential insurance fraud.

A potential benefit of the medical classification system 110 for clinicians is that clinicians may be able to spend less time double-checking their notes to determine patient outcomes. A doctor can therefore save time spent with administrative tasks and spend more time focused on patients. Another benefit is that the medical classification system 110 can help a doctor avoid forgetting their bilateral procedures, including procedures performed on two sides of the body. Further, by virtue of analyzing radiology reports and clinical events, the medical classification system 110 can help clinicians and other providers capture radiology events, lab events, and medical supplies that are typically not billed. More generally, the increased accuracy of billing codes can enhance clinician or insurer collections.

Because medical billing can be more accurate and collections enhanced, insurers can reduce deductibles and/or insurance premiums for patients. Additionally, the medical classification system 110 can enable medical services or supplies to be grouped together for better pricing of medical services.

Moreover, the medical classification system 110 can help reduce transposition of digits that can occur with manual coding and duplication of claims. Because the medical classification system 110 analyzes the structured clinical event data, the medical classification system 110 can also overcome billing errors that occur due to faulty dictation of clinician notes.

In some embodiments, the automatically-detected billing codes can also be used to train clinicians or staff to more accurately detect billing codes manually, should they be required to do so.

It should also be noted that if hand-tuning of weights is used, double counting can occur with correlated features in the data. In other words, if two rules are correlated so as to indicate the same outcome, hand-selection of these weights can account for this correlation by halving the weights for each feature. Advantageously, in certain embodiments, the machine learning algorithms described herein can automatically account for correlated features and generate appropriate weights accordingly. This automatic accounting occurs as a result of the properties of solving the optimization problem using MLE or other techniques.

VI. Terminology

Many other variations than those described herein will be apparent from this disclosure. For example, depending on the embodiment, certain acts, events, or functions of any of the algorithms described herein can be performed in a different sequence, can be added, merged, or left out all together (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines and/or computing systems that can function together. Although certain computer-implemented tasks are described as being performed by a particular entity, other embodiments are possible in which these tasks are performed by a different entity.

The various illustrative logical blocks, modules, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can also be implemented as a combination of computing devices, e.g., a combination of a DSP and a microprocessor, a plurality of microprocessors, one or more microprocessors in conjunction with a DSP core, or any other such configuration. A computing environment can include any type of computer system, including, but not limited to, a computer system based on a microprocessor, a mainframe computer, a digital signal processor, a portable computing device, a personal organizer, a device controller, and a computational engine within an appliance, to name a few.

The steps of a method, process, or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An exemplary storage medium can be coupled to the processor such that the processor can read information from, and write information to, the storage medium. In the alternative, the storage medium can be integral to the processor. The processor and the storage medium can reside in an ASIC. The ASIC can reside in a user terminal. In the alternative, the processor and the storage medium can reside as discrete components in a user terminal.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Terms used herein such as "optimize," "minimize," "maximize," and the like may, in addition to having their ordinary meaning, can denote attempts to optimize, minimize, or maximize one or more parameters or processes while potentially not fully optimizing, minimizing, or maximizing the parameters or processes. For instance, although a parameter or process may be referred to as being "optimized" herein, the parameter or process may be improved over some prior state and not actually reach an optimal solution. Similarly, a quantity that is "minimized" or "maximized" may be reduced or increased less than a fully minimal or maximal amount, respectively.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments of the inventions described herein can be embodied within a form that does not provide all of the features and benefits set forth herein, as some features can be used or practiced separately from others.

What is claimed is:

1. A system for classifying a health condition of a patient, the system comprising:

a model creation engine configured to create a medical classification model by at least:

receiving an identification of a clinical feature that is to be associated with a health condition, the identification being provided by one or more of an automated analysis of an electronic medical reference and a manual expert identification of the clinical feature, the clinical feature comprising one or more of the following features: an identified medication, a clinical event, a microbial culture feature, and a radiology feature, creating a rule that maps the clinical feature to the health condition in a model data repository comprising physical computer storage, wherein the rule reflects a relationship between the clinical feature and the health condition, automatically learning a weight to apply to the rule with a supervised machine learning algorithm by at least analyzing the clinical feature with respect to pre-identified outcomes in a training data set, the training data set comprising first structured clinical event data, the rule reflecting a strength of the relationship between the clinical feature and the health condition, and storing, in the model data repository, the learned weight associated with the rule for subsequent usage in identifying a patient health condition; and an outcome identification module comprising computer hardware, the outcome identification module configured to at least:

access patient data corresponding to a patient, the patient data comprising second structured clinical event data stored in an electronic health record (EHR) database, analyze the second structured clinical event data to determine whether the clinical feature exists in the clinical event data, apply the rule and the weight of the medical classification model to the clinical feature to infer a possible health condition of the patient by at least matching the rule with a selected clinical feature in the second structured clinical event data corresponding to the patient, and provide one or more billing codes configured to be processed by a medical billing system, said one or more billing codes being based at least in part on the possible health condition of the patient.

2. The system of claim 1, wherein the outcome identification module is further configured to apply the rule to infer the possible health condition of the patient by at least combining a count of occurrences of the clinical feature in the second structured clinical event data with the learned weight in a probabilistic function.

3. The system of claim 2, wherein the probabilistic function comprises a weighting function comprising one or more parameters derived from optimizing an objective on the training data.

4. The system of claim 3, wherein the weighting function comprises a logistic regression function.

5. The system of claim 1, wherein the model creation engine is further configured to incorporate a language-based rule and an associated weight in the model data repository.

6. The system of claim 5, wherein the outcome identification module is further configured to identify a language feature in clinician notes and to apply the language-based rule to the identified language feature as part of inferring the possible health condition of the patient.

7. The system of claim 1, wherein the outcome identification module infers the possible health condition of the patient by directly identifying the one or more billing codes.

8. The system of claim 1, wherein the machine learning algorithm comprises a supervised algorithm or a semi-supervised algorithm.

9. The system of claim 8, wherein the machine learning algorithm comprises one or more of the following: a maximum likelihood estimation algorithm, a support vector machine, a boosting algorithm, and a neural network algorithm.

10. The system of claim 1, wherein the electronic medical reference comprises an online medical dictionary.

* * * * *

UNITED STATES PATENT AND TRADEMARK OFFICE
CERTIFICATE OF CORRECTION

Page 1 of 1

PATENT NO. : 8,504,392 B2
APPLICATION NO. : 13/294959
DATED : August 6, 2013
INVENTOR(S) : Saria et al.

It is certified that error appears in the above-identified patent and that said Letters Patent is hereby corrected as shown below:

Title Page 1 (item 75, Inventors) at lines 4-5, Change "Daphne L. Koller" to --Daphne Koller--.

In the Drawings

Sheet 6 of 8 (Reference Numeral 400, FIG. 4) at line 5, Change "Dyslapsia" to --Dysplasia--.

Sheet 6 of 8 (Reference Numeral 400, FIG. 4) at line 10, Change "Stahylococcus" to --Staphylococcus--.

Sheet 6 of 8 (Reference Numeral 400, FIG. 4) at line 12, Change "Bacterimia" to --Bacteremia--.

In the Specification

In column 4 at line 45, Change "that that" to --that--.

In column 4 at line 64, Change "1008" to --100B--.

In column 7 at line 37, Change "LCPH," to --LPCH,--.

In column 15 at line 15, Change "w," to --wl--.

Signed and Sealed this
Eleventh Day of March, 2014

Michelle K. Lee
*Deputy Director of the United States Patent and Trademark Office*